(12) United States Patent
Ban et al.

(10) Patent No.: US 10,758,158 B2
(45) Date of Patent: Sep. 1, 2020

(54) SYSTEM AND METHOD FOR REHABILITATION EXERCISE OF THE HANDS

(71) Applicant: NEOFECT CO., LTD., Yongin-si, Gyeonggi-do (KR)

(72) Inventors: Hoyoung Ban, Yongin-si (KR); Younggeun Choi, Yongin-si (KR); Soobin Lee, Seongnam-si (KR); Kyunghwan Yoo, Incheon (KR); Sungjun Roh, Seoul (KR); Hoyeong Song, Yongin-si (KR)

(73) Assignee: NEOFECT CO., LTD., Yongin-si (KR)

( * ) Notice: Subject to any disclaimer, the term of this patent is extended or adjusted under 35 U.S.C. 154(b) by 15 days.

(21) Appl. No.: 16/172,347

(22) Filed: Oct. 26, 2018

(65) Prior Publication Data

US 2019/0059789 A1    Feb. 28, 2019

Related U.S. Application Data

(63) Continuation of application No. 14/879,212, filed on Oct. 9, 2015, now Pat. No. 10,143,403.

(30) Foreign Application Priority Data

Jan. 23, 2015 (KR) .................. 10-2015-0011145

(51) Int. Cl.
*A61B 5/11* (2006.01)
*A61B 5/00* (2006.01)
*G06F 3/01* (2006.01)

(52) U.S. Cl.
CPC .............. *A61B 5/11* (2013.01); *A61B 5/1125* (2013.01); *A61B 5/6824* (2013.01);
(Continued)

(58) Field of Classification Search
CPC ....... A61B 5/11; A61B 5/6824; A61B 5/1125; A61B 5/6831; A61B 5/6826;
(Continued)

(56) References Cited

U.S. PATENT DOCUMENTS

| 4,988,981 A | 1/1991 | Zimmerman et al. |
| 5,715,834 A | 2/1998 | Bergamasco et al. |

(Continued)

FOREIGN PATENT DOCUMENTS

| JP | 2002-345861 A | 12/2002 |
| KR | 10-1219990 B1 | 1/2013 |
| KR | 10-1263129 B1 | 5/2013 |

OTHER PUBLICATIONS

Korean Notice of Allowance dated Apr. 29, 2015 in connection with the counterpart Korean Patent Application No. 10-2015-0011145, citing the above reference(s).

*Primary Examiner* — Sundhara M Ganesan
(74) *Attorney, Agent, or Firm* — Studebaker & Brackett PC

(57) ABSTRACT

Disclosed are a system and a method for rehabilitation exercise of hands. The system and the method help a device sense movements of the hands more accurately. The device for rehabilitation exercise of the hands comprising multiple sense parts that are located on each part of a user's hand, and configured to sense movements of the each part; and communication part configured to send movement data sensed by the multiple sense parts to an output device.

6 Claims, 13 Drawing Sheets

(52) U.S. Cl.
CPC .......... *A61B 5/6825* (2013.01); *A61B 5/6826* (2013.01); *A61B 5/6831* (2013.01); *G06F 3/014* (2013.01); *A61B 5/0024* (2013.01); *A61B 5/1124* (2013.01); *A61B 5/744* (2013.01); *A61B 5/746* (2013.01); *A61B 2505/09* (2013.01); *A61B 2562/0219* (2013.01); *A61B 2562/0223* (2013.01); *A61B 2562/166* (2013.01)

(58) Field of Classification Search
CPC ............ A61B 5/6825; A61B 2562/166; A61B 2562/0223; A61B 5/0024; A61B 5/746; A61B 5/744; A61B 2562/0219; A61B 2505/09; A61B 5/1124; G06F 3/014; A61H 2201/5043; A61H 2201/5058; A61H 2201/5048; A61H 1/0285
See application file for complete search history.

(56) References Cited

U.S. PATENT DOCUMENTS

| | | |
|---|---|---|
| 6,454,681 B1 | 9/2002 | Brassil et al. |
| 2010/0234182 A1 | 9/2010 | Hoffman et al. |
| 2011/0267042 A1 | 11/2011 | Sano et al. |
| 2012/0029399 A1 | 2/2012 | Sankai |
| 2012/0157263 A1 | 6/2012 | Sivak et al. |
| 2012/0172682 A1 | 7/2012 | Linderman et al. |
| 2013/0060166 A1 | 3/2013 | Friedman et al. |
| 2013/0197399 A1 | 8/2013 | Montgomery |
| 2014/0074179 A1 | 3/2014 | Heldman et al. |
| 2014/0200432 A1 | 7/2014 | Banerji et al. |
| 2014/0240214 A1 | 8/2014 | Liu et al. |
| 2016/0089571 A1 | 3/2016 | Wesley et al. |
| 2016/0187973 A1 | 6/2016 | Shankar et al. |
| 2016/0284236 A1 | 9/2016 | Bavunoglu et al. |

SYSTEM AND METHOD FOR REHABILITATION EXERCISE OF THE HANDS

CROSS-REFERENCE TO RELATED APPLICATION

The present application is a continuation of U.S. patent application Ser. No. 14/879,212, filed on Oct. 9, 2015, which claims priority from Korean Patent No. 10-2015-0011145, filed on Jan. 23, 2015 in the Korean Intellectual Property Office. The disclosures of the above parent application and Korean Patent are incorporated herein by reference in its entirety.

TECHNICAL FIELD

The system and method for rehabilitation exercise of hands are disclosed.

RELATED ART

The statements in this section merely provide information related to the present disclosure and do not necessarily constitute prior art.

The purpose of the device for rehabilitation exercise of the hands is to help patients with paralysis/hemi-paralysis do rehabilitation exercise of the hands. When the patient wearing the device for rehabilitation exercise of the hands moves his hand, the device senses the movement of the hand and the doctor or the therapist refers to the sensing result of the device for rehabilitation exercise of the hands and adjusts the intensity or types of rehabilitation exercise appropriately.

In order to sense the movement of the hands, each part of the device for rehabilitation exercise of the hands is equipped with a bend sensor. This bend sensor has characteristics of changing resistance values in line with the bending information.

However, as can be seen in existing devices, if a bend sensor is used only, the accuracy level of sensing results gets lowered and it is not easy to sense subtle movements of the hands.

SUMMARY

One or more exemplary embodiments provide a system and method for rehabilitation exercise of the hands that help the device sense the movements of the hands more accurately.

Additional aspects of the exemplary embodiments will be set forth in part in the description which follows and, in part, will be obvious from the description, or may be learned by practice of the exemplary embodiments.

In accordance with an aspect of some embodiments, there is provided a device for rehabilitation exercise of the hands comprising: multiple sense parts that are located on each part of user's hand which to sense movements of the each part; and communication part that sends movement data sensed by the multiple sense parts to an output device wherein the multiple sense parts include sense parts for the multiple fingers including a first phalange sense part and a second phalange sense part that are located on a first phalange and a second phalange of users fingers respectively, a sense part for the back of the hand that is located on the back of user's hand, and a sense part for the wrist that is located on user's wrist, wherein fixing tools are placed on at least one of the multiple sense parts for the fingers, the sense part for the back of the hand, and the sense part for the wrist to fix the each sense parts on their corresponding parts, wherein the first phalange sense part is connected to the sense part for the back of the hand via a first connection part and the second phalange sense part is connected to the first phalange sense part via a second connection part, wherein some of the lines that are included in the first connection part are used as an antenna for wireless communication with the output device.

In accordance with an aspect of an another exemplary embodiment, there is provided a device for rehabilitation exercise of the hands comprising: multiple sense parts located on each part of user's hand which to sense movements of the each part; and communication part that sends movement data sensed by the multiple sense parts to an output device wherein the multiple sense parts include sense parts for the multiple fingers located on each finger of the user, a sense part for the back of the hand located on the back of user's hand, and a sense part for the wrist located on the wrist of the user, wherein fixing tools are located in at least one of the sense parts for the multiple fingers, the sense part for the back of the hand, and the sense part for the wrist in order to fix the each sense parts on their corresponding parts, wherein the fixing tools located on the sense part for the back of the hand include a first fixing part that wraps the palm to fix the sense part for the back of the hand on the back of the hand; and a second fixing part of which the one end is connected to the first fixing part and the other end, to the adherence part, wherein the adherence part is located on a first connection part that connects a first phalange sense part located on the first phalange of the thumb to the sense part for the back of the hand and can move along the first connection part.

BRIEF DESCRIPTION OF THE DRAWINGS

The above and/or other aspects will become apparent and more readily appreciated from the following description of exemplary embodiments, taken in conjunction with the accompanying drawings of which.

DETAILED DESCRIPTION

Figure 1:
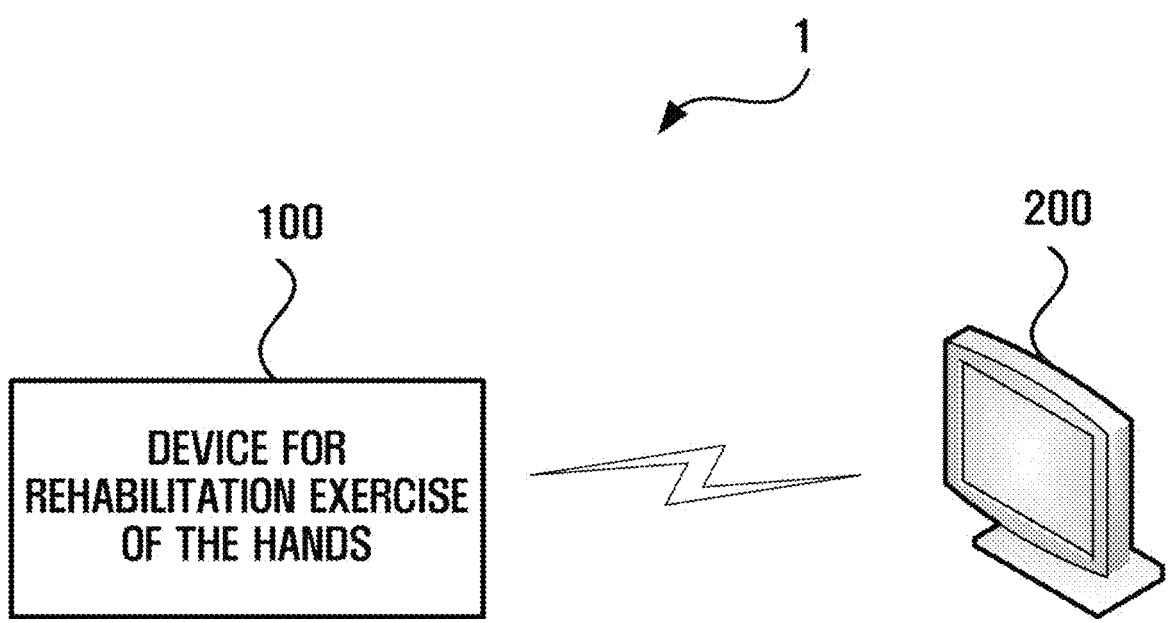
FIG. 1 illustrates a conceptual diagram of a composition of a system for rehabilitation exercise of hands, according to some embodiments of the present disclosure.

Reference will now be made in detail to exemplary embodiments, examples of which are illustrated in the accompanying drawings. However, the present inventive concept may be embodied in many different forms and should not be construed as being limited to the exemplary embodiments set forth herein. Rather, these exemplary embodiments are provided so that the present disclosure will be thorough and complete, and will fully convey the scope of the present inventive concept to those skilled in the art, and the spirit and scope of the present inventive concept should be defined by the appended claims.

Without separate definitions, all terms (including technical and scientific terms) used in the present description may be used for the meanings commonly understandable to those having ordinary skill in the art. In addition, the terms generally used and having definitions in dictionary, unless otherwise defined obviously in particular, should not be ideally or exaggeratedly interpreted.

The terms used in the present description are to explain the exemplary embodiments, not to limit the present invention thereto. In the present description, a singular form of word also includes a plural form thereof unless otherwise noted. The term "comprises" and/or "comprising" is not excluding the meaning that one or more elements other than the said element may exist or be added.

Hereinafter, exemplary embodiments of the present inventive concept will be described in detail with reference to the accompanying drawings. In the drawings, like reference numerals refer to like elements.

FIG. 1 illustrates a conceptual diagram of a composition of a system for rehabilitation exercise of hands, according to some embodiments of the present disclosure.

Referring to FIG. 1, the system for rehabilitation exercise of the hands (1) in accordance with one exemplary embodiment includes the device for rehabilitation exercise of the hands (100) and the output device (200).

The device for rehabilitation exercise of the hands (100) can be put on the hands of the user and sense the movements of the hands. Here, the user means the person or patient who needs rehabilitation exercise of the hands. The hands include fingers, the back of the hand, and the wrist. Thus, the movements of hands include the movements of the fingers, the back of the hand, and the wrist. Also sensing the movements of the fingers, the back of the hand, and the wrist means sensing the positions of the fingers, the back of the hand, and the wrist as well as the speed of movements and the direction of movements.

Figure 2:
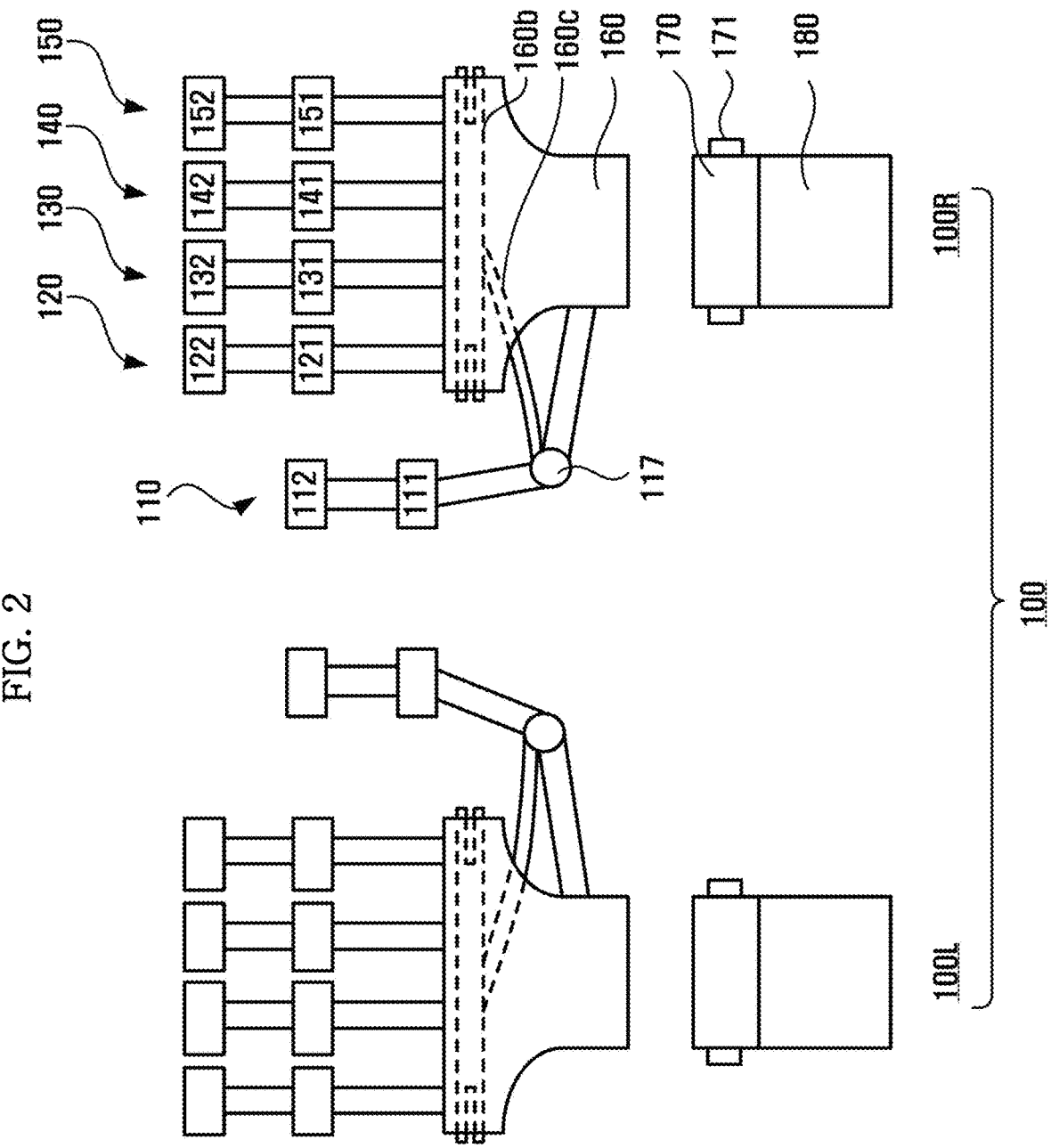
FIG. 2 is a schematic drawing of a device for rehabilitation exercise of a left hand and a device for rehabilitation exercise of a right hand, according to some embodiments of the present disclosure.

According to the exemplary embodiment, the device for rehabilitation exercise of the hands (100) includes at least one of the device for rehabilitation exercise of the left hand (see 100L of FIG. 2) and the device for rehabilitation exercise of the right hand (see 100R of FIG. 2). The device for rehabilitation exercise of the left hand (100L) is put on the left hand of the user and senses the movements of the left hand. And the device for rehabilitation exercise of the right hand (100R) is put on the right hand of the user and senses the movements of the right hand. The movement data of the hands that are sensed by the device for rehabilitation exercise of the left hand (100L) and/or the device for rehabilitation exercise of the right hand (100R) are sent to the output device (200). At this moment, the movement data of the hands are transmitted to the output device (200) via a wired communication method or a wireless communication method. The body of the device for rehabilitation exercise of the left hand (100L) and the body of the device for rehabilitation exercise of the right hand (100R) can be made of silicone. More detailed explanations about the device for rehabilitation exercise of the left hand (100L) and/or the device for rehabilitation exercise of the right hand (100R) will be described later in reference with FIG. 2, FIG. 3, and FIG. 4.

The output device (200) provides menus related to rehabilitation exercise of the hands. According to the exemplary embodiment, the menus related to rehabilitation exercise of the hands include user profile menu, game menu, exercise result menu, and configuration menu.

The user profile menu allows the entry of user data that are required for rehabilitation exercise of the hands. For example, the user profile includes name, gender, age, and medical history.

The game menu displays the list of games related to rehabilitation exercise of the hands. When the list of games is displayed, the user selects a game from the displayed list of games that he/she wants and does rehabilitation exercise of the hands, while playing the game.

The exercise result menu allows the user to check the result of rehabilitation exercise of the hands. The result of rehabilitation exercise of the hands may include at least one of duration of rehabilitation exercise of the hands, count of hand movements, speed of hand movements, and direction of hand movements. The duration of rehabilitation exercise of the hands refers to the time spent on rehabilitation exercise of the hands. And the movements of the hands may include downwards flexion of the wrist, upwards extension of the wrist, radial flexion of the wrist in the left direction, and ulnar flexion of the wrist in the right direction, rotation of the wrist, finger flexion, and wrist extension. According to the exemplary embodiment, the results of rehabilitation exercise of the hands can be provided by the game or integrated regardless of the games.

In the configuration menu, information related to various movement statuses of the output device (200) can be set.

Meanwhile, when a game is selected from the list of games related to rehabilitation exercise of the hands, the output device (200) configures the game screen based on the movement data of the left and/or right hand that are received from the device for rehabilitation exercise of the hands (100), and outputs the results of the game.

According to the exemplary embodiment, the output device (200) receives the movement data of the left and/or right hand from the device for rehabilitation exercise of the hands (100), according to a wired communication method or a wireless communication method. The wireless communication methods include NFC (Near Field Communication), Wireless USB, UWB (Ultra Wide Band), Wi-Fi, Bluetooth, ZIGBEE, RF (Radio Frequency), and IrDA (Infrared Data Association).

When the output device (200) communicates with the device for rehabilitation exercise of the hands (100) according to the wireless communication method, a pairing process can be performed between the output device (200) and the device for rehabilitation exercise of the hands (100). Paring is the process of registering device information of the output device (200) in the device for rehabilitation exercise of the hands (100) and registering the device information of the device for rehabilitation exercise of the hands (100) in the output device (200). After pairing is completed between the two devices (100, 200), security can be enhanced for data that are transmitted between the two devices (100, 200). However, the pairing process between the two devices (100, 200) is not required and it can be skipped in some cases.

When the movement data of the left hand and/or the right hand are received from the device for rehabilitation exercise of the hands (100), the output device (200) configures a screen that includes the hand movement data received and displays the data as a visual signal. The screen can be shown while a program or a game to help rehabilitation exercise of the user's hands is run. The screen can be configured as a two-dimensional image, a three-dimensional image, an actual image, an augmented reality image, or the combination of the aforementioned images.

According to the exemplary embodiment, graphic objects (See FIG. 7 and FIG. 9 400) corresponding to the movement data of the hands are placed in the screen. When all of the movement data of the left hand and the movement data of the right hand are received from the device for rehabilitation exercise of the hands (100), the screen displays graphic objects corresponding to the movement data of the left hand and the graphic objects corresponding to the movement data of the right hand. When the left hand and/or right hand of the user move continuously, the corresponding object(s) are moving continuously as well.

Meanwhile, the program or the game to help rehabilitation exercise of user's hands are ended, the output device (200) can send the result of rehabilitation exercise of the hands as at least one of a visual signal and an audio signal. The result of rehabilitation exercise of the hands can be stored in the output device (200) or can be transmitted to an external device (not illustrated) according to the wired communication method or the wireless communication method.

As described above, the output device (200) may include wired/wireless communication devices. Communication devices include a cellular phone, a PCS (Personal Communication Service) phone, a mobile device of IMT-2000 (International Mobile Telecommunication-2000), a Palm PC (Personal Computer), a PDA (Personal Digital Assistant), a smart phone, a WAP (Wireless Application Protocol) phone, and a mobile game device.

Also the output device (200) can be a wearable device that can be put on the body of the user, for example, the head or the face. To this end, the output device (200) may take the form of a helmet or glasses. However, the external feature of the output device (200) is not limited to the aforementioned forms and it may take a flexible form.

So far, in reference with FIG. 1, the system for rehabilitation exercise of the hands (1) in accordance with one exemplary embodiment is illustrated. The device for rehabilitation exercise of the hands (100) and/or the output device (200) can be a device owned by the user or a device owned by a professional medical institute like a hospital or a rehabilitation centre.

Hereinafter, the appearance and composition of the device for rehabilitation exercise of the hands (100) are explained more in reference with FIG. 2, FIG. 3, and FIG. 4.

FIG. 2 is a schematic drawing of the device for rehabilitation exercise of the left hand (100L) and the device for rehabilitation exercise of the right hand (100R), according to some embodiments. FIG. 3 is a schematic drawing of the device for rehabilitation exercise of the right hand (100R) that is put on the hand, according to some embodiments. FIG. 4 is a schematic block diagram of the device for rehabilitation exercise of the right hand (100R), according to some embodiments.

As explained above, the device for rehabilitation exercise of the hands (100) may include the device for rehabilitation exercise of the left hand (100L) and the device for rehabilitation exercise of the right hand (100R). The device for rehabilitation exercise of the left hand (100L) and the device for rehabilitation exercise of the right hand (100R) basically have same components but the difference is that each component is placed symmetrically. Therefore, the appearance and composition are explained based on the device for rehabilitation exercise of the right hand (100R).

Figure 3:
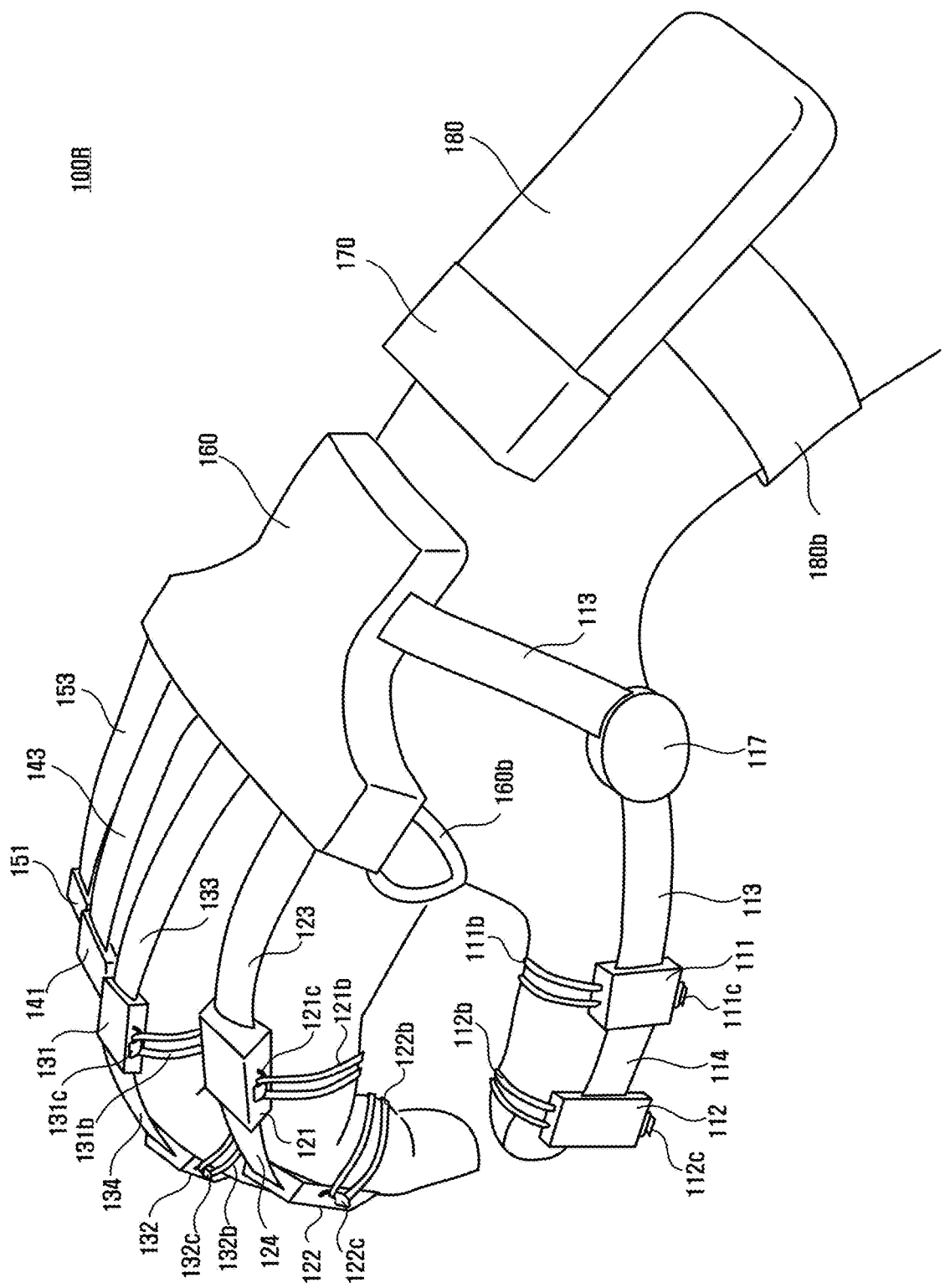
FIG. 3 is a schematic drawing of a device for rehabilitation exercise of a right hand that is put on the right hand, according to some embodiments of the present disclosure.
Figure 4:
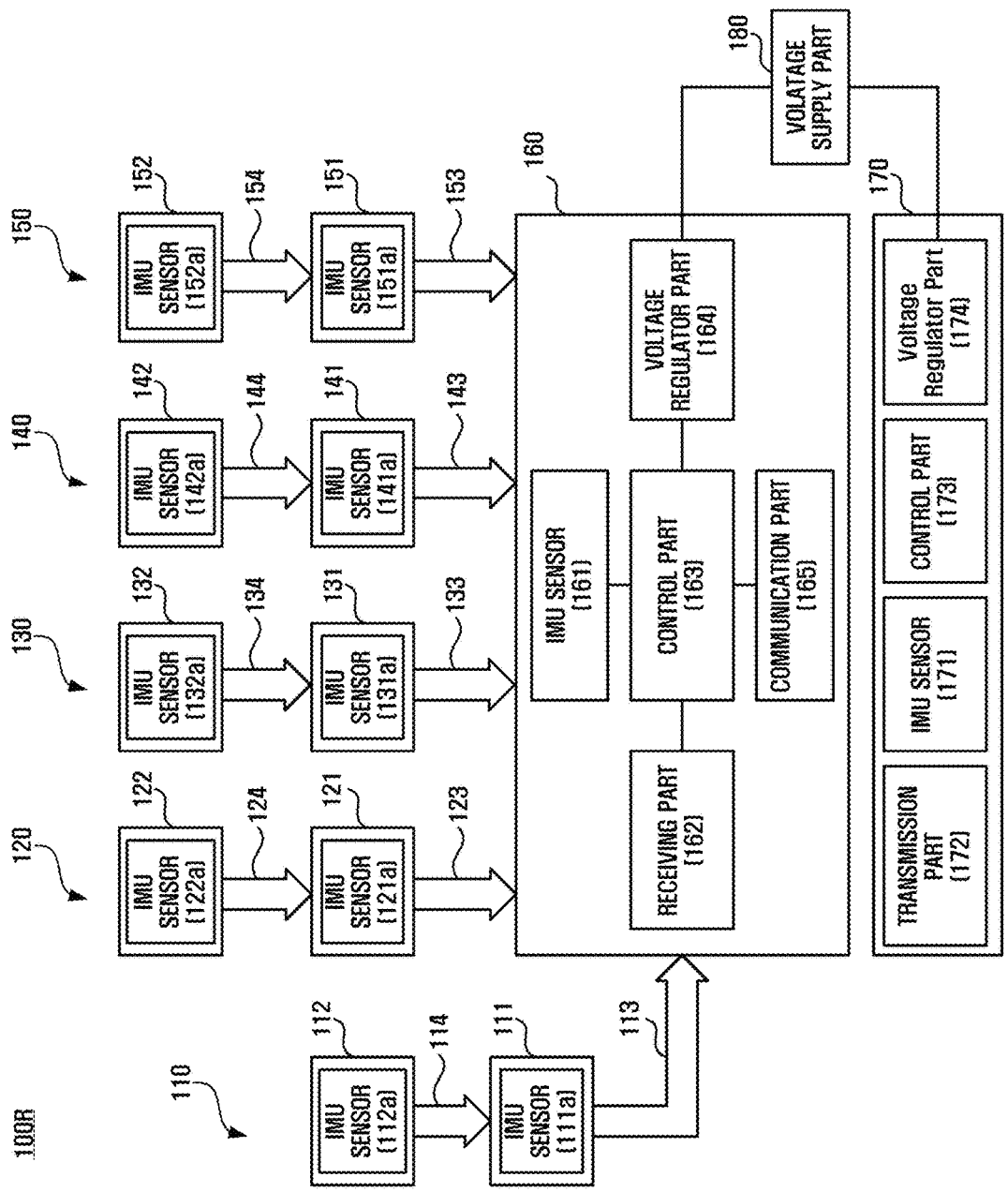
FIG. 4 is a schematic block diagram of a device for rehabilitation exercise of a right hand, according to some embodiments of the present disclosure.

Referring to FIG. 2, FIG. 3, and FIG. 4, the device for rehabilitation exercise of the right hand (100R) includes the multiple sense parts for the fingers (110, 120, 130, 140, 150), the sense part for the back of the hand (160), the sense part for the wrist (170), and the voltage supply part (180).

The voltage supply part (180) supplies voltage to each of the sense parts (110, 120, 130, 140, 150, 160, 170). The voltage supply part (180) may include, for example, a battery. As illustrated in FIG. 2 and FIG. 3, the voltage supply part (180) can be combined with the sense part for the wrist (170) mechanically.

According to one exemplary embodiment, the voltage supply part (180) can be embodied in a way that it can be separated from the sense part for the wrist (170) mechanically. When the combining tools (171) located on both sides of the sense part for the wrist (170) are pressed at the same time, the voltage supply part (180) is separated from the sense part for the wrist (170). In this case, the voltage supply part (180) that is separated from the sense part for the wrist (170) can be replaced with other voltage supply part (not illustrated) or connected electrically to a separate charge device (not illustrated) for charging. When this happens, the voltage supply part (180) can be provided with electricity from the charge device, according to a wired power transmission technology or a wireless power transmission technology.

According to another exemplary embodiment, the voltage supply part (180) can be implemented to be mechanically united with the sense part for the wrist (170) to be an all-in-one part. In this case, the voltage supply part (180) can be charged by an external power supply source. For example, the voltage supply part (180) can be charged by a wired charge method. To this end, an insert groove (not illustrated), where a charge cable's terminal is inserted, can be placed. In another example, the voltage supply part (180) can be charged by a wireless charge method. To this end, a wireless power receiving part (not illustrated) to receive electricity wirelessly from the power supply source can be placed on the voltage supply part (180).

The battery included in the voltage supply part (180) can be a general battery that is not bendable or a flexible battery that can be bended like paper. According to some embodiments, the voltage supply part (180) is located in an area that has little or no impact on rehabilitation exercise of user's hands. In one exemplary embodiment, the voltage supply part (180) can be placed on the back of the arm near user's wrist as can be seen in FIG. 3. According to some embodiments, the voltage supply part (180) can be embedded with the fixing tool (180*b*) that fixes the voltage supply part (180) on user's arm. The fixing tool (180*b*) may take the form of a loop to wrap part of the back of the arm or a ring where the user can put his/her arm through. Such a fixing tool (180b) can be made of elastic materials or stretchable materials.

The multiple sense parts for the ringers (110, 120, 130, 140, 150) include the thumb sense part (110), the index finger sense part (120), the middle finger sense part (130), the ring finger sense part (140), and the little finger sense part (150). Each of the sense parts (110, 120, 130, 140, 150) is composed of the first phalange sense parts (111, 121, 131, 141, 151) and the second phalange sense parts (112, 122, 132, 142, 152).

The first phalange parts (111, 121, 131, 141, 151) are located on the proximal phalanges of each finger. As described in FIG. 3, the first phalange parts (111, 121, 131, 141, 151) have the fixing tools (111b, 111c, 121b, 121c, 131b, 131c) that fix the first phalange sense parts (111, 121, 131, 141, 151) to the proximal phalanges of each finger.

As described in FIG. 3, each of the fixing tools (111b, 111c, 121b, 121c, 131b, 131c) include the fixing strings (111b, 121b, 131b) and the fixing hangers (111c, 121c, 131c).

The fixing strings (111b, 121b, 131b) are located on one side of the first phalange sense parts (111, 121, 131). The fixing hangers (111c, 121c, 131c) are located on other side of the first phalange sense parts (111, 121, 131). After wrapping the proximal phalange of each finger with the fixing strings (111b, 121b, 131b) and hanging the ends of the fixing strings (111b, 121b, 131b) on the fixing hangers (111c, 121c, 131c), the first phalange sense parts (111, 121, 131) can be contacted to the corresponding parts. Here, the fixing strings (111b, 121b, 131b) can be made of elastic materials or stretchable materials. If the fixing strings (111b, 121b, 131b) are made of elastic materials or stretchable materials, the first phalange sense parts (111, 121, 131) can be very closed to the corresponding parts regardless of thickness of fingers.

FIG. 3 illustrates the fixing tools (111b, 111c, 121b, 121c, 131b, 131c) that consist of the fixing strings (111b, 121b, 131b) and the fixing hangers (111c, 121c, 131c). However, the fixing tools can take different forms. For example, fixing tools may take the form of a loop to wrap part of the circumference of the proximal phalange of each finger or the form of a ring to put each finger through. Such fixing tools can be made of elastic materials, for example, rubber, or stretchable materials.

The first phalange sense parts (111, 121, 131, 141, 151) described above sense movements of the proximal phalanges of each finger. To this end, as described in FIG. 4, the first phalange sense parts (111, 121, 131, 141, 151) include IMU (Inertial Measurement Unit) sensors (111a, 121a, 131a, 141a, 151a) mounted on the printed circuit board.

The IMU sensors (111a, 121a, 131a, 141a, 151a) can be 9-axis IMU sensors based on MEMS (Micro Mechanical System). The 9-axis IMU sensors are composed of a 3-axis acceleration sensor, a 3-axis gyroscope sensor, and a 3-axis terrestrial magnetism sensor. The 3-axis acceleration sensor measures movement inertia (acceleration) of axes x, y, and z. The 3-axis gyroscope sensor measures rotation inertia (velocity) of axes x, y, and z. The 3-axis terrestrial magnetism sensor measures azimuth (direction of terrestrial magnetism) of axes x, y, and z.

According to another exemplary embodiment, the first phalange sense parts (111, 121, 131, 141, 151) may include at least one of the acceleration sensor and gyroscope sensor instead of the IMU sensor. In one exemplary embodiment, the first phalange sense parts (111, 121, 131, 141, 151) may include the acceleration sensor only. In another exemplary embodiment, the first phalange sense parts (111, 121, 131, 141, 151) may include the acceleration sensor and the gyroscope sensor.

The first phalange sense parts (111, 121, 131, 141, 151) are connected to the sense part for the back of the hand (160) via the first connection parts (113, 123, 133, 143, 153). In some embodiments, a connector (not illustrated) is located on the printed circuit board of the first phalange sense parts (111, 121, 131, 141, 151) and one ends of the first connection parts (113, 123, 133, 143, 153) are connected to this connector. The other ends of the first connection parts (113, 123, 133, 143, 153) are connected to the connector (not illustrated) that is located on the printed circuit board of the sense part for the back of the hand (160).

According to some embodiments, at least one of the length, shape, and materials of the first connection parts (113, 123, 133, 143, 153) can be decided in a way that they do not hinder the movements of fingers.

In one exemplary embodiment, the length of the first connection parts (113, 123, 133, 143, 153) can be longer than the distance between the first phalange sense parts (111, 121, 131, 141, 151) and the sense part for the back of the hand (160) and be twisted like a telephone wire. In this case, when the user bends his/her fingers while wearing the device for rehabilitation exercise of the right hand (100R), the twisted part of the first connection parts (113, 123, 133, 143, 153) is stretched and therefore, does not interrupt the movement of the finger.

In another example, the length of the first connection parts (113, 123, 133, 143, 153) can be similar to the distance between the first phalange sense parts (111, 121, 131, 141, 151) and the sense part for the back of the hand (160) but can be made of stretchable materials. In some embodiments, the first connection parts (113, 123, 133, 143, 153) can be made of stretchable optical fibre cables. In this case, when the user bends his/her fingers while wearing the device for rehabilitation exercise of the right hand (100R), the length of the first connection parts (113, 123, 133, 143, 153) is prolonged naturally by elasticity and therefore, the movements of the fingers are not hindered.

In another example, the first connection parts (113, 123, 133, 143, 153) can be made of materials without elasticity but made longer than the distance between the first phalange sense parts (111, 121, 131, 141, 151) and the sense part for the back of the hand (160). For example, the first connection parts (113, 123, 133, 143, 153) can be about 1.5 times longer than the distance between the first phalange sense parts (111, 121, 131, 141, 151) and the sense part for the back of the hand (160). However, the length of the first connection parts (113, 123, 133, 143, 153) does not have to be same as the length in the examples and the length is advised to be determined in consideration of the average length of fingers of diverse users.

According to some embodiments, the first connection parts (113, 123, 133, 143, 153) can be separated from the printed circuit board of the first phalange sense parts (111, 121, 131, 141, 151) and the printed circuit board of the sense part for the back of the hand (160). Therefore, if any of the first phalange sense parts (111, 121, 131, 141, 151) breaks down, the malfunctioning part of the first phalange sense parts (111, 121, 131, 141, 151) can be replaced easily and quickly. Furthermore, as only the malfunctioning part of the first phalange sense parts (111, 121, 131, 141, 151) is to be replaced instead of replacing the device for rehabilitation exercise of the right hand (100R), the device can be operated more economically.

According to some embodiments, the first connection parts (113, 123, 133, 143, 153) may include multiple lines. The multiple lines can be divided into a data line, a voltage line, and an antenna line, depending on their functions.

The data lines refer to the lines that are used to transmit the data measured by the IMU sensors (111*a*, 121*a*, 131*a*, 141*a*, 151*a*) of the first phalange sense parts (111, 121, 131, 141, 151) to the sense part for the back of the hand (160). The voltage lines are used to supply voltage to the first phalange sense parts (111, 121, 131, 141, 151). The antenna lines are the lines that are used as antenna for wireless communications between the device for rehabilitation exercise of the right hand (100R) and the output device (200).

As such, some of the multiple lines of the first connection parts (113, 123, 133, 143, 153) are used as an antenna for wireless communications with the output device (200) and therefore, the length of the first connection parts (113, 123, 133, 143, 153) can be determined in consideration of such purposes.

The second phalange sense parts (112, 122, 132, 142, 152) are placed on the distal phalange of the thumb and the middle phalanges of the rest of the fingers. According to some embodiments and as can be seen in FIG. 3, the fixing tools (112*b*, 112*c*, 122*b*, 122*c*, 132*b*, 132*c*) are placed in the second phalange sense parts (112, 122, 132, 142, 152) in order to fix the second phalange sense parts (112, 122, 132, 142, 152) to the corresponding phalange of each finger.

As shown in FIG. 3, the fixing tools (112*b*, 112*c*, 122*b*, 122*c*, 132*b*, 132*c*) include the fixing strings (112*b*, 122*b*, 132*b*) and the fixing hangers (112*c*, 122*c*, 132*c*).

The fixing strings (112*b*, 122*b*, 132*b*) are placed on one side of the second phalange sense parts (112, 122, 132). The fixing hangers (112*c*, 122*c*, 132*c*) are placed on other side of the second phalange sense parts (112, 122, 132). After wrapping the first phalange of each finger with the fixing strings (112*b*, 122*b*, 132*b*) and hanging one ends of the fixing strings (112*b*, 122*b*, 132*b*) to the fixing hangers (112*c*, 122*c*, 132*c*), the second phalange sense parts (112, 122, 132) can be contacted to the corresponding parts. Here, the fixing strings (112*b*, 122*b*, 132*b*) can be made of elastic materials or stretchable materials. If the fixing strings (112*b*, 122*b*, 132*b*) are made of elastic materials or stretchable materials, the second phalange sense parts (112, 122, 132) can be very closed to the corresponding parts regardless of the thickness of fingers.

According to another exemplary embodiment, the fixing tools may take the form of a loop to wrap part of the circumference of the second phalange of each finger or a ring to put each finger through. The fixing tools for a loop shape or a ring shape can be made of elastic materials, for example, rubber, or stretchable materials.

The second phalange sense parts (112, 122, 132, 142, 152) sense the movements of the distal phalange of the thumb and the middle phalanges of the rest of the fingers. To this end, the second phalange sense parts (112, 122, 132, 142, 152) includes the IMU sensors (112*a*, 122*a*, 132*a*, 142*a*, 152*a*) mounted on the printed circuit board as illustrated in FIG. 4. The IMU sensors (112*a*, 122*a*, 132*a*, 142*a*, 152*a*) can be a 9-axis IMU sensor based on MEMS.

According to another exemplary embodiment, the second phalange sense parts (112, 122, 132, 142, 152) may include at least one of the acceleration sensor and the gyroscope sensor. In one example, the second phalange sense parts (112, 122, 132, 142, 152) may include the acceleration sensor only. In another example, the second phalange sense parts (112, 122, 132, 142, 152) may include the acceleration sensor and the gyroscope sensor.

The second phalange sense parts (112, 122, 132, 142, 152) are connected to the first phalange sense parts (111, 121, 131, 141, 151) via the second connection parts (114, 124, 134, 144, 154). In some embodiments, a connector (not illustrated) is placed in the printed circuit board of the second phalange sense parts (112, 122, 132, 142, 152) and the connector is connected to one ends of the second connection parts (114, 124, 134, 144, 154). Other ends of the second connection parts (114, 124, 134, 144, 154) are connected to the connector (not illustrated) in the printed circuit board of the first phalange sense parts (111, 121, 131, 141, 151).

According to some embodiments, at least one of the length, shape, and materials of the second connection parts (114, 124, 134, 144, 154) can be determined in a way that they do not hinder the movements of the fingers. The length, shape, and materials of the second connection parts (114, 124, 134, 144, 154) will not be explained herein because they can be determined in the same way as the length, shape, and materials of the first connection parts (113, 123, 133, 143, 153) that are explained above.

According to some embodiments, the second connection parts (114, 124, 134, 144, 154) can be separated from the printed circuit board of the second phalange sense parts (112, 122, 132, 142, 152) and the printed circuit board of the first phalange sense parts (111, 121, 131, 141, 151). Therefore, if any of the second phalange sense parts (112, 122, 132, 142, 152) breaks down, the malfunctioning second phalange sense part can be replaced easily and quickly. Furthermore, as only the malfunctioning second phalange sense part can be replaced without having to replace the device for rehabilitation exercise of the right hand (100R), the device can be operated more economically.

According to some embodiments, the second connection parts (114, 124, 134, 144, 154) may include multiple lines. The multiple lines can be divided into a data line and a voltage line, depending on their functions.

The data lines are used to transmit the data measured by the IMU sensors (112*a*, 122*a*, 132*a*, 142*a*, 152*a*) of the second phalange sense parts (112, 122, 132, 142, 152). The data transmitted via the data lines of the second connection parts (114, 124, 134, 144, 154) are sent to the sense part for the back of the hand (160) via the printed circuit board of the first phalange sense parts (111, 121, 131, 141, 151). The voltage lines are used to supply voltage to the second phalange sense parts (112, 122, 132, 142, 152).

The sense part for the wrist (170) is located on the exterior of the wrist. Unlike the multiple sense parts for the fingers (110, 120, 130, 140, 150) that are explained above, there are no fixing tools in the sense part for the wrist (170). Because the sense part for the wrist (170) is combined with the voltage supply part (180) mechanically and the voltage supply part (180) itself is fixed on the back of the arm via the fixing tool (180*b*) mounted in the voltage supply part (180). Although not illustrated in drawings, according to another exemplary embodiment, more fixing tools can be placed in the sense part for the wrist (170) to fix the sense part for the wrist (170).

This sense part for the wrist (170) senses the movements of user's wrist and transmits the sensed data to the sense part for the back of the hand (160). To this end, as illustrated in FIG. 4, the sense part for the wrist (170) may include the IMU sensor (171), the transmission part (172), the control part (173), and the voltage control part (174). These components can be mounted in the printed circuit board.

The IMU sensor (171) senses the movements of the wrist. In some embodiments, the IMU sensor (171) can sense downwards flexion of the wrist, upwards extension of the wrist, radial flexion of the wrist in the left direction, ulnar flexion of the wrist in the right direction, and rotation of the wrist. The IMU sensor (171) can be a 9-axis IMU sensor based on MEMS. According to another exemplary embodiment, an acceleration sensor can be placed instead of the IMU sensor (171). In another exemplary embodiment, an acceleration sensor and a gyroscope sensor can be placed instead of the IMU sensor (171).

The transmission part (172) transmits the data detected in the IMU sensor (171) to the sense part for the back of the hand (160) via a wireless communication method. The wireless communication methods include NFC (Near Field Communication), wireless USB, UWB (Ultra Wide Band, Wi-Fi, Bluetooth, ZIGBEE, RF (Radio Frequency), and IrDA (Infrared Data Association). The case where the transmission part (172) transmits data via RF is explained below.

The control part (173) can connect and control each component of the sense part for the wrist (170). For example, when the IMU sensor (171) sense the movement of the wrist, the control part (173) controls the transmission part (172) and transmits the detected data to the sense part for the back of the hand (160).

The voltage regulator part (174) regulates the voltage level supplied by the voltage supply part (180) and supplies it to each component within the sense part for the wrist (170). In some embodiments, the voltage regulator part (174) lowers the level of voltage supplied from the voltage supply part (180) and supplies it to each component within the sense part for the wrist (170). Such a voltage regulator part (174) may include, for example, a low dropout regulator.

The sense part for the back of the hand (160) is placed on the back of user's hand. According to some embodiments and as shown in FIG. 2 and FIG. 3, fixing tools (160b, 160c) are located on the sense part for the back of the hand (160) in order to fix the sense part for the back of the hand (160) on the back of the hand.

The fixing tools (160b, 160c) may include the first fixing part (160b) and the second fixing part (160c). The first fixing part (160b) is to fix the sense part for the back of the hand (160) on the back of the hand and it may take the form of a loop to wrap part of the circumference of the palm or a ring to put the palm through. One end of the second fixing part (160c) is connected to the first fixing part (160b). The other end of the second fixing part (160c) is connected to the adherence part (117).

The adherence part (117) is located on the first connection part (113) that connects the first phalange sense part (111) of the thumb and the sense part for the back of the hand (160) and it can move along the first connection part (113). As such, when the adherence part (117) and the second fixing part (160c) are placed, the first connection part (113) can be adhered to the back of the hand. In some embodiments, since the adherence part (117) can move in line with the circumference of the back of user's hand, the first connection part (113) can be adhered to the back of the hand regardless of the circumference of the back of user's hand. However, the second fixing part (160c) and the adherence part (117) are not required and the second fixing part (160c) and the adherence part (117) can be omitted.

The sense part for the back of the hand (160) described above senses the movement of the back of user's hand. Also the sense part for the back of the hand (160) collects the data sensed in the sense part for the back of the hand (160), sense parts of multiple fingers (110, 120, 130, 140, 150), and the sense part for the wrist (170) and sends them to the output device (200). To this end, as described in FIG. 4, the sense part for the back of the hand (160) may include the IMU sensor (161), the receiving part (162), the control part (163), and the voltage regulator part (164), and the communication part (165). These components can be mounted in the printed circuit board.

The IMU sensor (161) senses the movement of the back of the hand. The IMU sensor (161) can be a 9-axis IMU sensor based on MEMS. According to another exemplary embodiment, an acceleration sensor can be placed instead of the IMU sensor (161). In another exemplary embodiment, an acceleration sensor and a gyroscope sensor can be placed instead of the IMU sensor (161).

The receiving part (162) pairs with the transmission part (172) of the sense part for the wrist (170) and it receives data sensed by the IMU sensor (171) of the sense part for the wrist (170) via RF.

The control part (163) can connect and control each component within the sense part for the back of the hand (160). For example, if the device for rehabilitation exercise of the right hand (100R) communicates with the output device (200) via a wireless communication method, the control part (163) controls each component and helps the device for rehabilitation exercise of the right hand (100R) pair with the output device (200). After pairing is completed, each IMU sensor (111a, 121a, 131a, 141a, 151a, 112a, 122a, 132a, 142a, 152a, 161, 171) senses the movement of the sense parts for multiple fingers (110, 120, 130, 140, 150), the sense part for the back of the hand (160), and the sense part for the wrist (170), the sensed data are collected and sent to the output device (200).

Also the control part (163) compares the data sensed by each sense part (110, 120, 130, 140, 150, 160, 170) with the reference movement data that are stored and if the sensed movement data are not consistent with the reference movement data it may output a notification signal to inform the user that user's hand movements are not up to the reference.

In some embodiments, the control part (163) is implemented by, or include(s), one or more processors and/or application-specific integrated circuits (ASICs) specified for respectively corresponding operations and functions described herein in the present disclosure.

The notification signal can be an audio signal, a touch signal, an optical signal, or a combination of these. To this end, an output part (not illustrated) can be equipped with the sense part for the back of the hand (160). The output part may include at least one of a speaker to send out an indication signal as an audio signal, a vibration output part to send out an indication signal as a tactile signal, and a light emitting diode to send out an indication signal as an optical signal. For example, the vibration output part may include a micro actuator.

According to another exemplary embodiment, the output part can be located not only in the sense part for the wrist (160) but also in each part of the hand. In some embodiments, the output part can be located around at least one of the sense parts for multiple fingers (110, 120, 130, 140, 150) and sense part for the wrist (170). If an output part is located around each sense part, a notification signal can be printed out per corresponding part.

So far, the control part (163) of the case where the sense part for the back of the hand (160) considers the movements of user's hands to be below the reference has been explained but such judgement can be made by the control part (230) of the output device (200) and a notification signal may output via the output part (220) of the output device (200).

Figure 5:
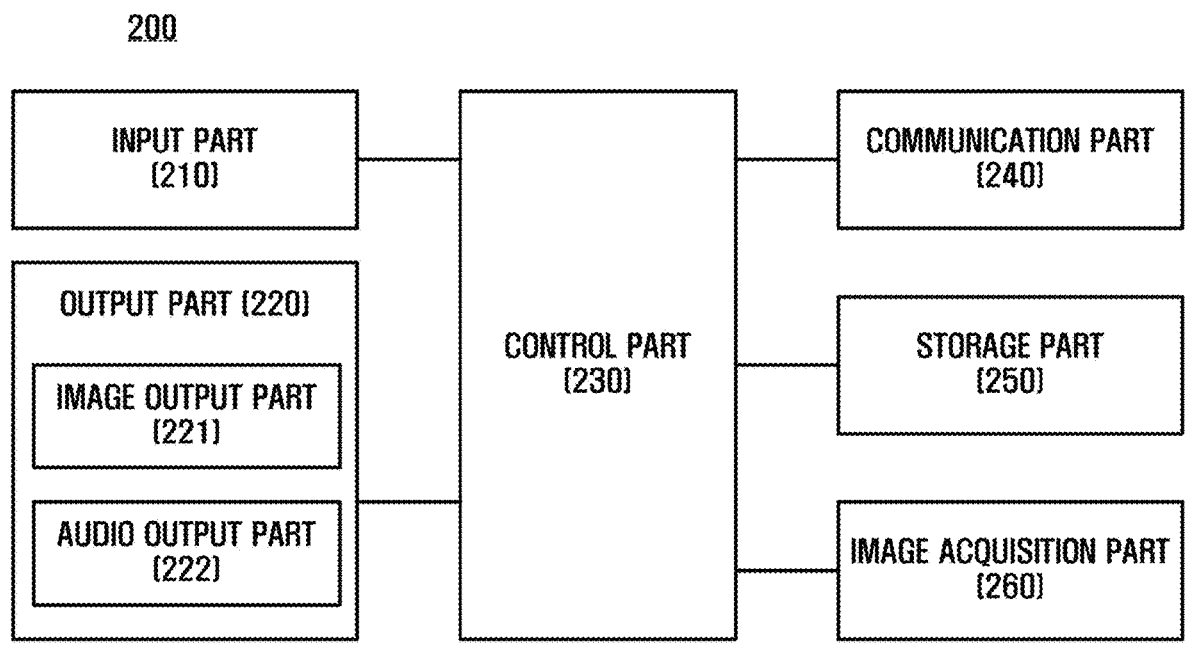
FIG. 5 is a schematic block diagram of a output device, according to some embodiments of the present disclosure.

FIG. 5 is a schematic block diagram of the output device (200), according to some embodiments.

Referring to FIG. 5, the output device (200) may include the input part (210), the output part (220), the control part (230), and the communication part (240), the storage part (250), and the image acquisition part (260).

The input part (210) receives user profile or commands from the user. The user profile may include the name, gender, age, and medical history of the user. The commands include a command to select a program or a game that is related to rehabilitation exercise of the hands, a command to run the selected program or game, a command to print out the result of rehabilitation exercise of the hands, a command to display a graphic object corresponding to the movement of the hands, and a command to change the view over the displayed graphic object.

The input part (210) may include input means such as mouse, keyboard, joy stick, touch pad, touch screen, or a combination of these. The key board can be implemented as hardware or software. Also the input part (210) consists of components of the output device (200) as shown in FIG. 5. In another example, the input part (210) can be implemented as a separate device that can communicate with the output device (200) via a wired communication method and/or a wireless communication method.

The output part (220) may output the result of command as a visual signal and/or an audio signal. To this end, the output part (220) may include an image output part (221) and an audio output part (222).

The image output part (221) output the result of command as a visual signal. For example, the image output part (221) output a screen that includes a graphic object corresponding to the hand movement data.

The screen may be a screen that displayed during execution of a program or a game to help rehabilitation exercise of user's hands. Also the screen may include a two-dimensional image, three-dimensional image, an actual image, or a combination of the said images.

The types of graphic objects can be determined in line with the types of screens. For example, if the screen is for two-dimensional images, the graphic objects corresponding to hand's movement data can be two dimensional. If the type of screen is for three-dimensional images, the graphic object corresponding to the hand's movement data can be a three-dimensional graphic object located in a virtual three-dimensional space. At this moment, the three-dimensional graphic object can be displayed as of the predefined view and the view can be modified according to the command entered by the user.

The image output part (221) may include a flat panel display, a flexible display, or a micro display. The flat panel display or the flexible display can be a non-transparent display or a transparent display. As an optical system display, the micro display can be located in HMD (Head Mounted Display). As described in FIG. 5, the image output part (221) can be part of the output device (200) or be implemented as a separate device that enables wired and/or wireless communications with the output device (200).

According to one exemplary embodiment, the image output part (221) may have output function only or both input and output functions. For example, if the image output part (221) is embodied as a touch screen, the image output part (221) has both input and output functions.

The audio output part (222) output the result of command as an audio signal. For example, the audio output part (222) may include a speaker.

FIG. 5 describes the case where the output part (220) includes an image output part (221) and an audio output part (222). In another exemplary embodiment, instead of the audio output part (222), the image output part (221) may include a vibration output part (not illustrated) to output the result of command as a tactile signal or an optical output part (not illustrated) to output the result of command as a light. Also it may include all of the image output part (221), the audio output part (222), the vibration output part, and the optical output part.

The communication part (240) transmits and receives a signal and/or data to and from the device for rehabilitation exercise of the hands (100). For example, the communication part (240) transmits and receives signals that are required to pair the output device (200) and the device for rehabilitation exercise of the hands (100). In another example, the communication part (240) receives hand movement data from the device for rehabilitation exercise of the hands (100). The received hand movement data are sent to the control part (230) that will be described later. Additionally, the communication part (240) can exchange signals and/or data with other external devices (not illustrated).

The storage part (250) can store data or an algorithm that are required to activate the output device (200). For example, the storage part (250) can store graphic data that are needed to configure screens related to a program or a game to help rehabilitation exercise of the hands, an algorithm to analyse the hand movement data received from the device for rehabilitation exercise of the hands (100), and user profile. The storage part (250) may include volatile memory, non-volatile memory, hard disc drive, optical disc drive, or a combination of these.

The image acquisition part (260) can obtain images. For example, if the appearance of the output device (200) takes the form of a HMD, the image acquisition part (260) can obtain actual images of the front of the user. The actual images obtained in the image acquisition part (260) can be used to configure augmented reality images matching the graphic objects on the actual images.

The control part (230) configures graphic objects corresponding to hand movement data or a screen including such graphic objects, based on the hand movement data received from the device for rehabilitation exercise of the hands (100). The control part (230) can configure the screen based on the graphic data stored in the storage part (250) or configure the screen based on actual images obtained from the image acquisition part (260). The configured graphic objects or screens are displayed via the image output part (221).

Also when the hand movement data received from the device for rehabilitation exercise of the hands (100) are not up to the reference movement data, the control part (230) output a notification message or a warning message via the output part (220), reading that the movement of user's hands is not up to the reference. Here, the notification message or the warning message may output as at least one of a visual signal, an audio signal, a touch signal, and an optical signal.

Also the control part (230) can analyse the hand movement data of the user and output a result of rehabilitation exercise of the hands. The result of rehabilitation exercise of the hands can be output via the output part (220) or transmitted to an external device (not illustrated) at the request of the user.

FIGS. 6, 7, 8, 9, 10 and 11 are drawings of exemplary movements of the device for rehabilitation exercise of the right hand (100R) and game screens to be displayed via the output device (200).

In accordance with some embodiments, the output device (200) can store diverse types of games related to rehabilitation exercise of the hands. For example, a game to help rehabilitation exercise of the wrist and a game to help rehabilitation exercise of fingers can be stored. Each game can be implemented to repeat hand movements. For example, the game can be implemented to repeat one of the movements like pouring water into a cup, catching a moving fish, catching a flying butterfly, using a fan, opening a bottle, catching a flying ball, turning over leaves (of a book), and painting a fence with a brush.

When the game list described above is displayed via the image output part (221) of the output device (200), the user can select a game that he/she needs or wants. If a game is selected, the control part (230) of the output device (200) configures a screen for the selected game. For example, if a game to repeat the movement to catch a ball is selected, the game screen (40) illustrated in FIG. 5 is displayed in the image output part (221) of the output device (200).

Figure 6:
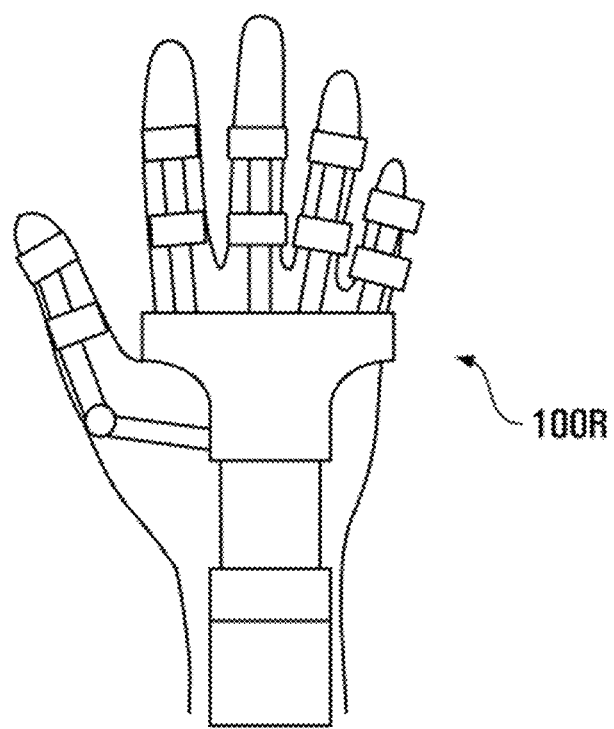
FIGS. 6, 7, 8, 9, 10 and 11 are schematic drawings of exemplary movements of a device for rehabilitation exercise of a right hand and game screens to be displayed via the output device, according to some embodiments of the present disclosure.
Figure 7:
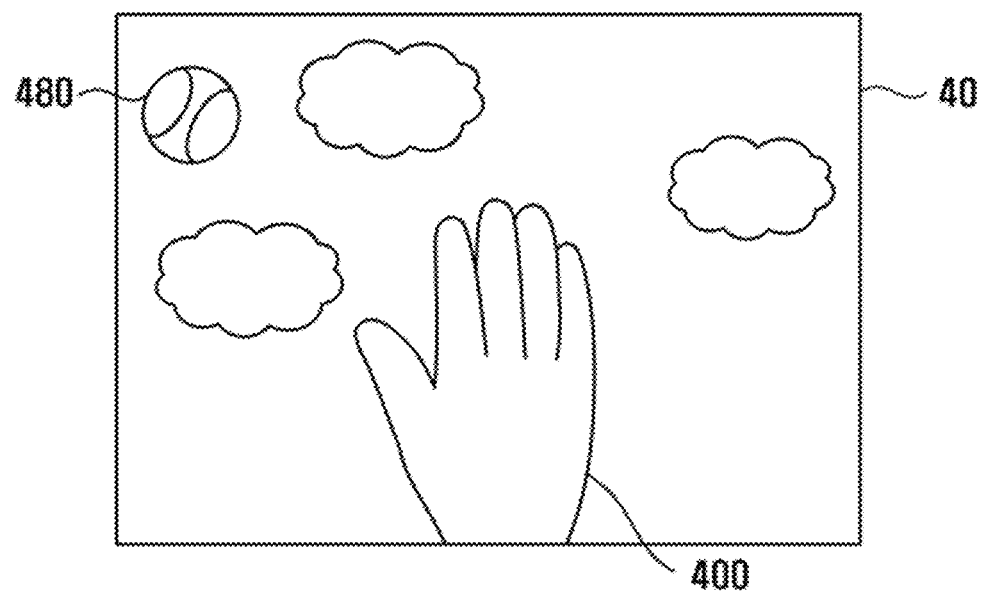
Figure 8:
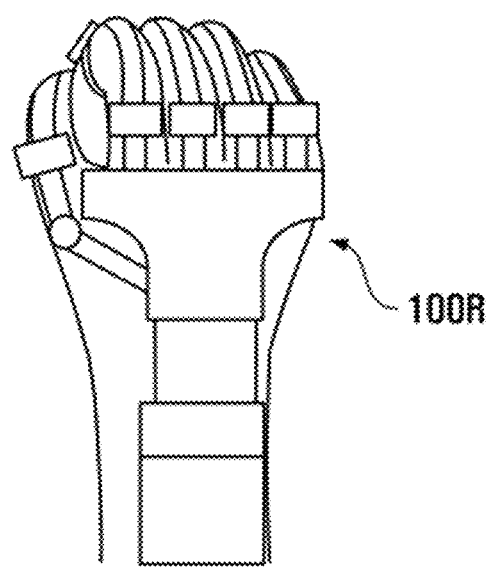

In reference with FIGS. 6 and 7, the ball-shaped graphic object (480) and the right hand-shaped graphic object (400) are placed in the game screen (40). The right hand-shaped graphic object (400) moves in response to the movements of the device for rehabilitation exercise of the right hand (100R). As shown in FIGS. 6 and 7, if all of the fingers of the device for rehabilitation exercise of the right hand (100R) are stretched, the right hand-shaped graphic object (400) displays stretched fingers.

In some embodiments, the control part (230) is implemented by, or include(s), one or more processors and/or application-specific integrated circuits (ASICs) specified for respectively corresponding operations and functions described herein in the present disclosure.

Figure 9:
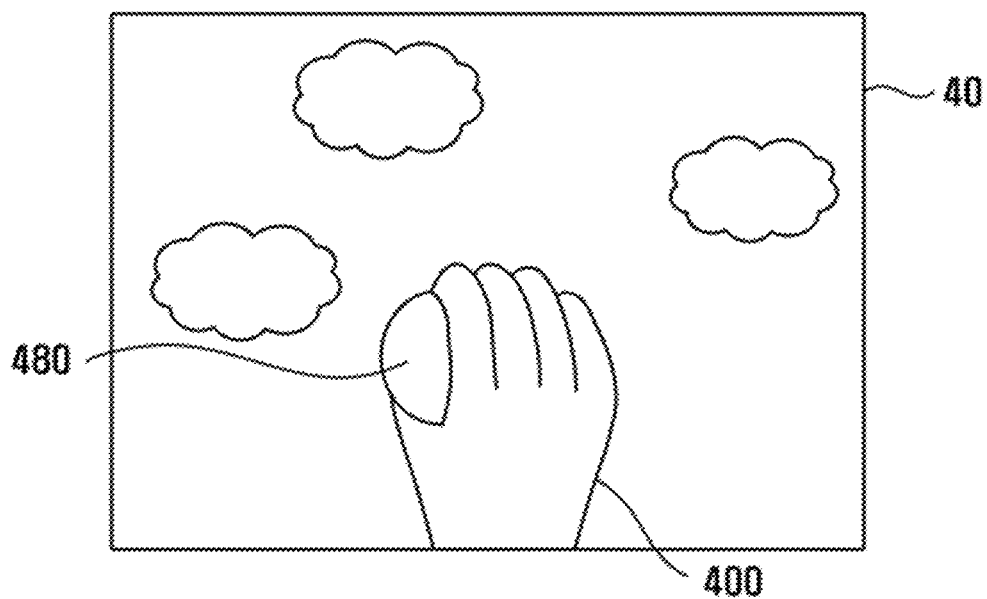
Figure 10:
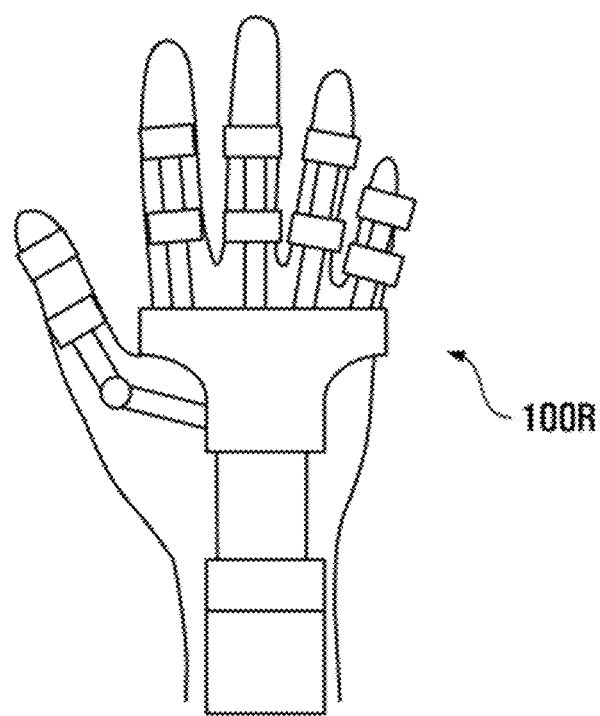

When a game is played, the ball-shaped graphic object (480) moves gradually towards the right hand-shaped graphic object (400). Upon checking the movement of the ball-shaped graphic object (480), the user makes a gesture of catching a ball. For example, as shown in FIGS. 9 and 10, if the user makes a gesture of bending all fingers, the sense parts of multiple fingers (110, 120, 130, 140, 150) of the device for rehabilitation exercise of the right hand (100R) that is put on each finger bend as well. As a result, the right hand-shaped graphic object (400) shows bended fingers.

If the user succeeds or fails in catching the ball-shaped graphic object (480), a success or failure message can be output via the output part (220) of the output device (200). The notification message can be printed out as a visual signal, an audio signal, a tactile signal, an optical signal, or a combination of these signals. Apart from the success in the game, additional information like the goal that the user has to achieve, success counts, and movement counts can be displayed in an area in the game screen.

So far, the examples of movements of the device for rehabilitation exercise of the right hand (100R) and the game screen (40) displayed via the output device (200) have been explained in reference with FIGS. 6, 7, 8 and 9. FIGS. 6, 7, 8 and 9 illustrate the game screens (40) in two dimensions but the types of game images are not limited hereto. According to another exemplary embodiment, game images can be three-dimensional images that are looked from a view to a virtual three-dimensional space. In this case, the ball-shaped graphic object (480) and the right hand-shaped graphic object (400) can be expressed as a three-dimensional graphic object and placed in the virtual three-dimensional space. According to another exemplary embodiment, the game image can be an AR (Augmented Reality) image matching the ball-shaped graphic object (380) or the right hand-shaped graphic object (400) on the actual image.

Also FIGS. 6, 7, 8 and 9 illustrate the case where the game screen (40) is displayed via the output device (200), however, the screen to be displayed via the output device (200; FIG. 5) is not limited to the game screen (40). For example, as shown in FIGS. 10 and 11, in the screen displayed via the output device (200), the right hand-shaped graphic object (500) corresponding to the movement of the device for rehabilitation exercise of the right hand (100R) can be displayed regardless of the game.

Figure 11:
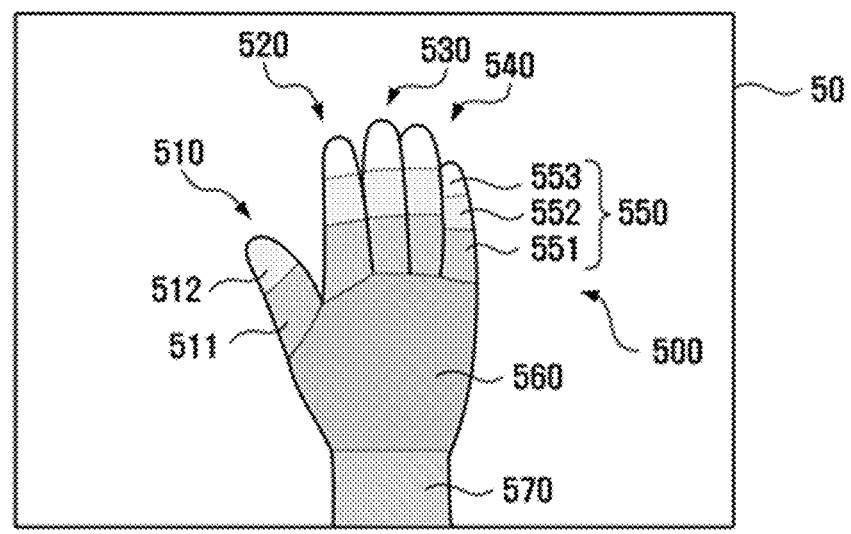

In accordance with one exemplary embodiment, the right hand-shaped graphic object (500) described in FIGS. 10 and 11 can be a two-dimensional graphic object. In accordance with another exemplary embodiment, the right hand-shaped graphic object (500) illustrated in FIGS. 10 and 11 can be a three-dimensional graphic object that is located in a virtual three-dimensional space. At this moment, the right hand-shaped three-dimensional graphic object is displayed from a view and the user can change views by touching the screen (50) and dragging it towards a direction. When views change, the right hand-shaped three-dimensional graphic object is displayed from the changed view. The aforementioned control part (230) can take care of command recognition to change views and graphic in line with the recognized command.

Referring to FIGS. 10 and 11, the right hand-shaped graphic object (500) can be divided into multiple areas according to the locations of each sense part (110, 120, 130, 140, 150, 160, 170) of the device for rehabilitation exercise of the right hand (100R). For example, the right hand-shaped graphic objects (500) can be divided into the finger areas (510, 520, 530, 540, 550), the back of the hand area (560), and the wrist area (570). According to some embodiments, these areas can be displayed as a different colour from each other.

Meanwhile, the finger areas (510, 520, 530, 540, 550) can be divided into the thumb area (510), the index finger area (520), the middle finger area (530), the ring finger area (540), and the little finger (550). The thumb area (510) can be divided into the first area (511) corresponding to the proximal phalange and the second area (512) corresponding to the distal phalange. Except for the thumb area (510) the areas of the rest of fingers (520, 530, 540, 550) can be divided into the first area (551) corresponding to each proximal phalange, the second area (552) corresponding to the middle phalange, and the third area (553) corresponding to the distal phalange. In the areas of each finger (510, 520, 530, 540, 550), the first area (551), the second area (552), and the third area (553) are displayed in different colours. In the areas of each finger (510, 520, 530, 540, 550), the first areas (511, 551) can be displaced in the same colour while the second areas (512, 552) can be displayed in the same colour in the areas of each finger (510, 520, 530, 540, 550). As such, if the first area (551), the second area (552), and the third area (553) are displayed in different colours, the user can recognize the movements of each part intuitively.

Figure 12:
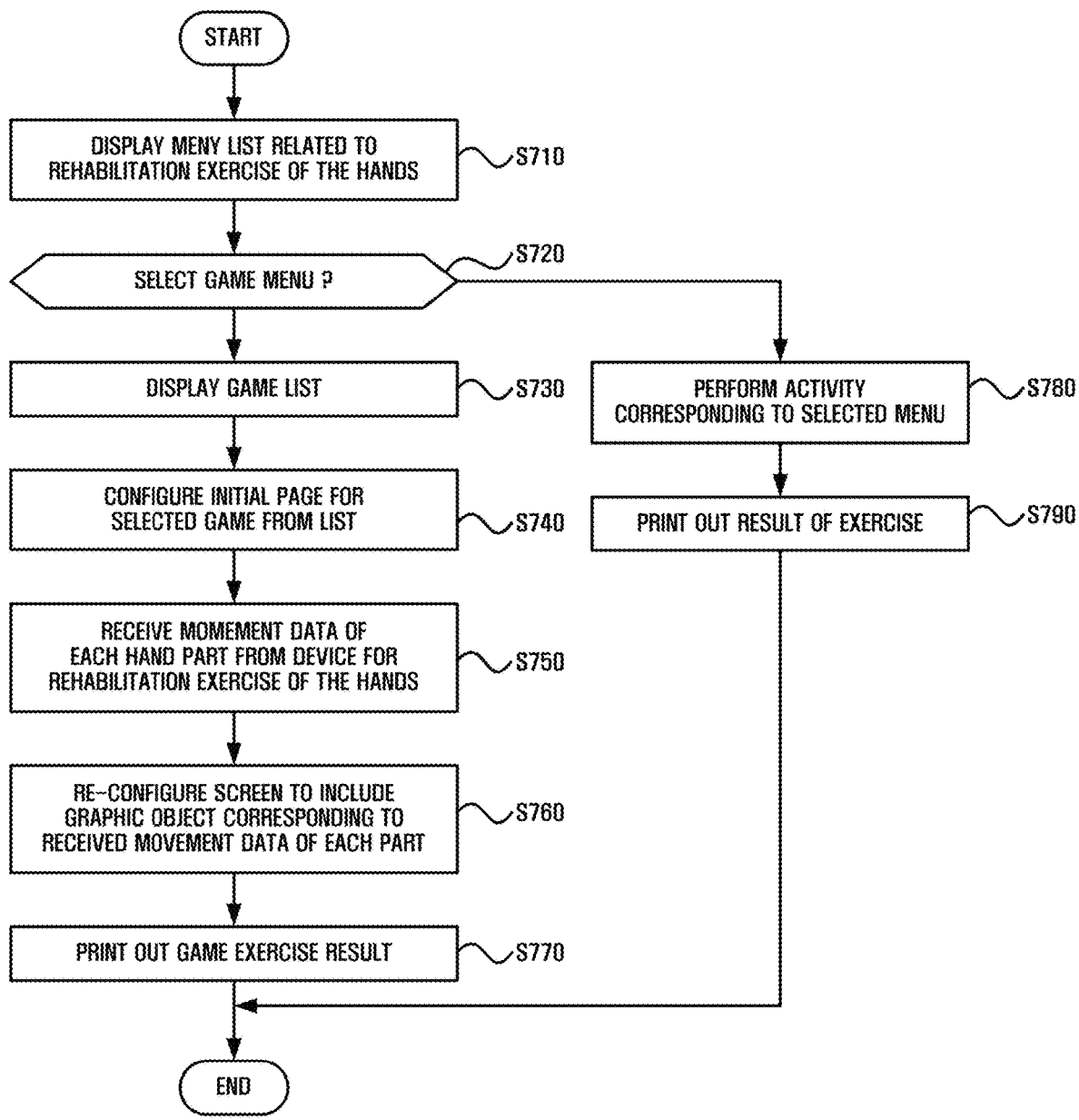
FIG. 12 is a flowchart of a method of rehabilitation exercise of hands using a system for rehabilitation exercise of the hands, according to some embodiments of the present disclosure.

FIG. 12 is a flowchart of the method of rehabilitation exercise of the hands using the system for rehabilitation exercise of the hands (1), according to some embodiments of the present disclosure.

In some embodiments, procedures of the method according to this disclosure, to be discussed hereinafter are implemented and stored in a computer-executable recording medium which is executed by a processor and/or an ASIC of the device described in FIG. 5.

Before explanation, it is assumed that the device for rehabilitation exercise of the hands (100) and the output device (200) exchange signals and/or data via a wireless communication method and that the pairing process between the device for rehabilitation exercise of the hands (100) and the output device (200) is completed. Also it is assumed that the user is wearing the device for rehabilitation exercise of the left hand (100L) and/or the device for rehabilitation exercise of the right hand (100R).

First, the output device (200) displays a menu list related to rehabilitation exercise for the hands, in operation S710. The menu related to rehabilitation exercise of the hands includes user profile menu, game menu, result of rehabilitation exercise menu, and configuration menu.

After that, the output device (200) confirms whether a game menu is selected from the displayed menu, in operation S720.

If the game menu is selected in operation S720, the output device (200) displays the list of games via the image output part (221), in operation S730. In other words, the list of games to help rehabilitation exercise of the hands is displayed.

If a game is selected from the displayed game list, the output device (200) configures the initial screen of the selected game, in operation S740. For example, if a game to repeat the movement of catching a ball is selected, the game screen including the ball-shaped graphic object (480) and the hand-shaped graphic object (400) is configured as shown in FIG. 7. The configured game screen (40) is displayed via the image output part (221).

While the game is played, the ball-shaped graphic object (480) moves inside the screen. After that, if the user makes a gesture of catching a ball, the movement data of each part of the hand are detected by multiple sense parts (110, 120, 130, 140, 150, 160, 170) of the device for rehabilitation exercise of the hands (100). The movement data of each part of the hand that have been detected are sent to the output device (200).

The output device (200) receives the movement data of each part of the hand from the device for rehabilitation exercise of the hands (100), in operation S750.

Then the output device (200) reconfigures a screen to include a graphic object (400) that corresponds to the received movement data of each part of the hands, in operation S760. In other words, a screen is reconfigured in a way that the hand-shaped graphic object (400) corresponds to the movement data of each part of the hands that are received from the device for rehabilitation exercise of the hands (100).

After that, the output device (200) output the result of the game, in operation S770. That is, it output a message indicating whether the user succeeds or fails in catching the moving ball-shaped graphic object (480). Here, the indication message may output as a visual signal, an audio signal, a touch signal, an optical signal, or a combination of these.

Meanwhile, if the game menu is not selected in operation S720, the output device (200) performs an activity that corresponds to the selected menu, in operation S780. And the output device (200) output the result of the performed activity, in operation S790. For example, if the menu of exercise result is selected out of the menus related to rehabilitation exercise of the hands, the output device (200) output the result of rehabilitation exercise of the hands. The operation S780 may include the operation to output the result of rehabilitation exercise of the hands per game. The result of rehabilitation exercise of the hands may include at least one of the duration of rehabilitation exercise of the hands, the count of hand exercise, the speed of hand exercise, and the direction of hand exercise.

So far, the system for rehabilitation exercise of the hands and the method for rehabilitation exercise of the hands in accordance of one exemplary embodiment have been explained in reference with FIG. 1 or FIG. 12. According to one exemplary embodiment, each of the sense parts for multiple fingers (110, 120, 130, 140, 150) include the first phalange sense part (111, 121, 131, 141, 151) and the second phalange sense parts (112, 122, 132, 142, 152) only and the case where the sense part for the back of the hand (160) and the sense part for the wrist (170) are communicated with each other via a wireless communication method has been explained. However, this invention is not limited hereto.

According to another exemplary embodiment, except for the thumb sense part (110), the index finger sense part (120), the middle finger sense part (130), the ring finger sense part (140), and the little finger sense part (150) may include the first phalange sense part, the second phalange sense part, and the third phalange sense part, respectively. For more detailed explanation, FIG. 13, FIG. 14, and FIG. 15 will be referenced.

Figure 13:
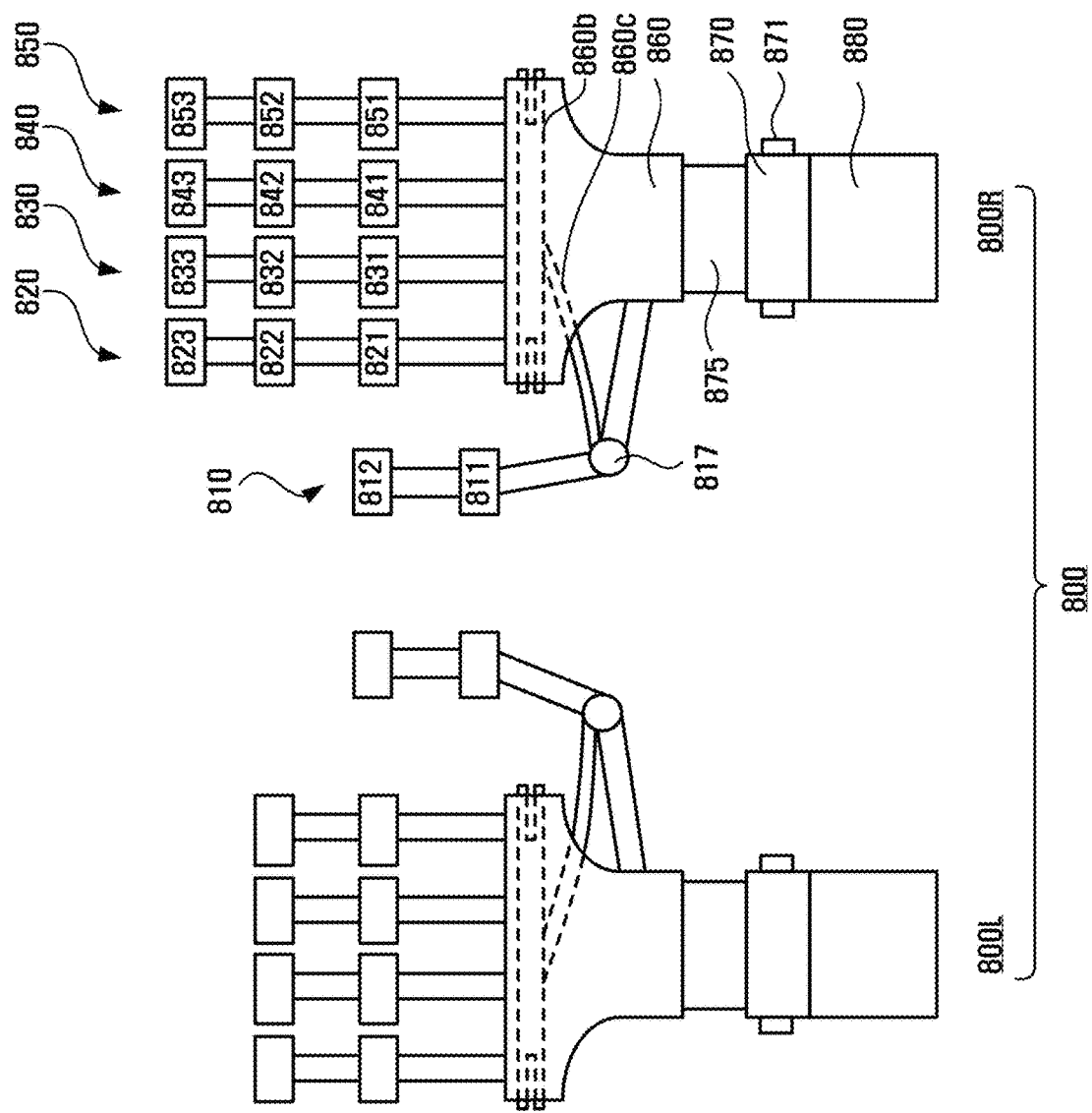
FIG. 13 is a schematic drawing of a device for rehabilitation exercise of a left hand and a device for rehabilitation exercise of a right hand, according to some embodiments of the present disclosure.
Figure 14:
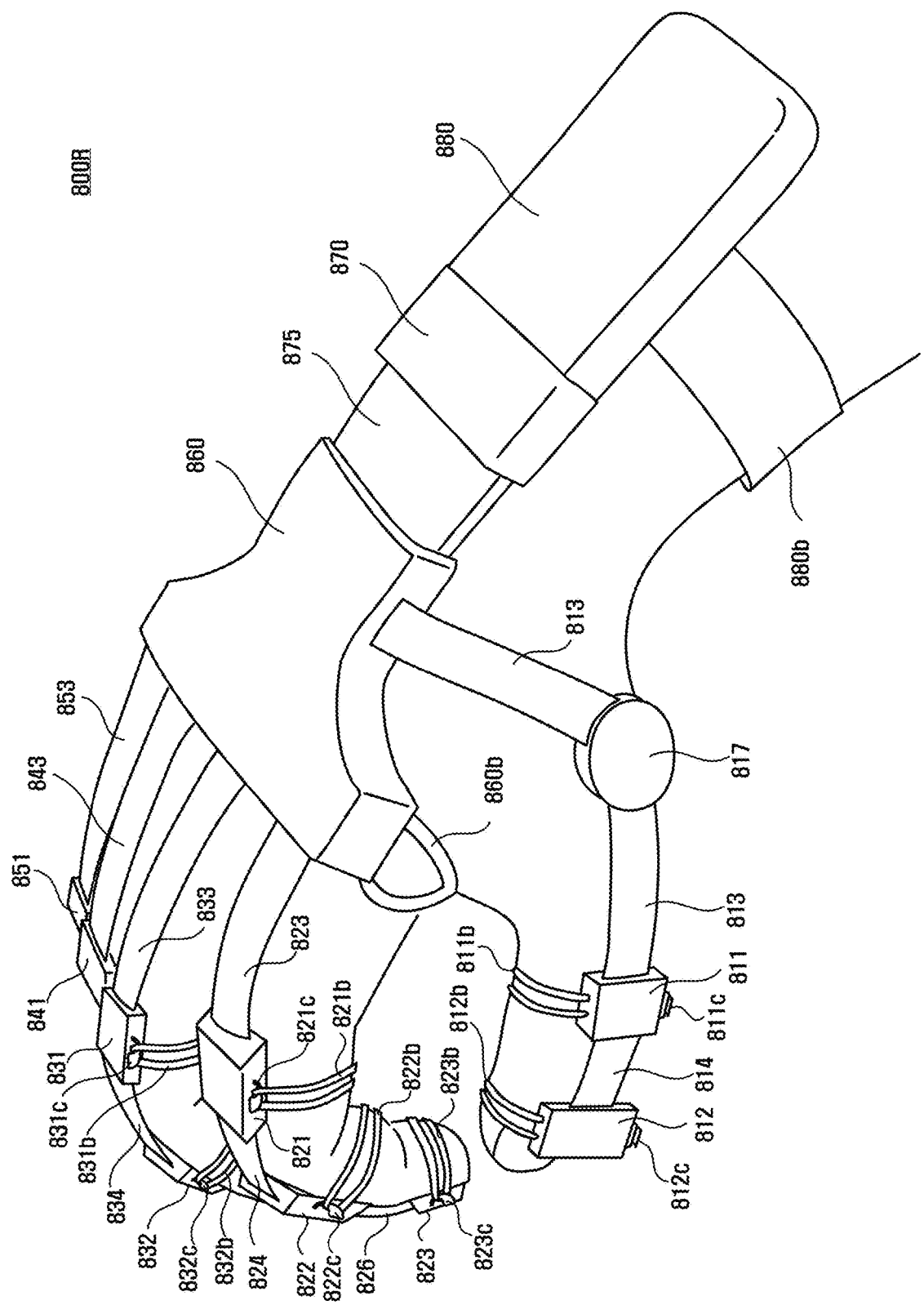
FIG. 14 is a schematic drawing illustrating a device for rehabilitation exercise of a right hand that is put on the right hand, according to some embodiments of the present disclosure.
Figure 15:
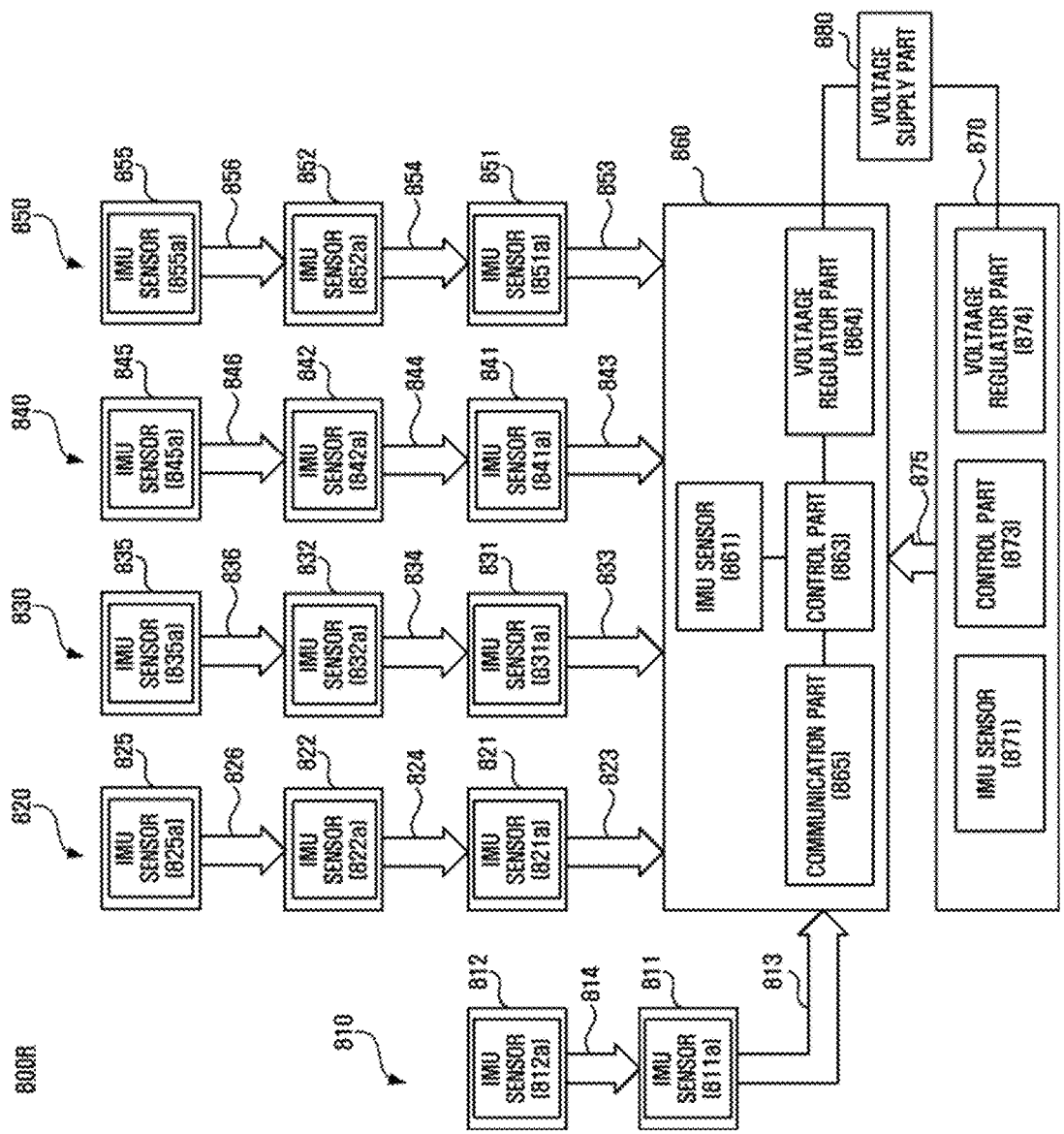
FIG. 15 is a schematic block diagram of a device for rehabilitation exercise of a right hand, according to some embodiments of the present disclosure.

FIG. 13 is a schematic drawing of the device for rehabilitation exercise of the left hand (800L) and the device for rehabilitation exercise of the right hand (800R) in accordance with another exemplary embodiment. FIG. 14 is a schematic drawing of the hand wearing the device for rehabilitation exercise of the right hand (800R). FIG. 15 is a schematic block diagram of the device for rehabilitation exercise of the right hand (800R).

The device for rehabilitation exercise of the hands (800) in accordance with another exemplary embodiment may include the device for rehabilitation exercise of the left hand (800L) and the device for rehabilitation exercise of the right hand (800R) and the explanation or the appearance and composition will be given based on the device for rehabilitation exercise of the right hand (800R). Also the device for rehabilitation exercise of the right hand (800R) illustrated in FIG. 13 and FIG. 14 is almost similar to the device for rehabilitation exercise of the right hand (100R) illustrated in FIG. 2 and FIG. 3 in terms of appearance and composition. Therefore, the explanation will skip the duplicate part and focus on differences.

In reference with FIG. 13 and FIG. 14, the device for rehabilitation exercise of the right hand (800R) includes the sense parts for multiple fingers (810, 820, 830, 840, 850). The sense parts for multiple fingers (810, 820, 830, 840, 850) include the thumb sense part (810), the index finger sense part (820), the middle finger sense part (830), the ring finger sense part (840), and the little finger sense part (850).

The thumb sense part (810) includes the first sense part (811) and the second sense part (812). In comparison, the index finger sense part (820), the middle finger sense part (830), the ring finger sense part (840), and the little finger sense part (850) include the first phalange sense parts (821, 831, 841, 851), the second phalange sense parts (822, 832, 842, 852), and the third phalange sense parts (823, 833, 843, 853), respectively.

The first phalange sense parts (821, 831, 841, 851) are located on the proximal phalanges of each finger of the user. The second phalange sense parts (822, 832, 842, 852) are located on the middle phalanges of each finger of the user. And the third phalange sense parts (823, 833, 843, 853) are located on the distal phalanges of each finger of the user.

The third phalange sense parts (823, 833, 843, 853) include fixing tools (823*b*, 823*c*). As illustrated in FIG. 14, the fixing tools (823*b*, 823*c*) include the fixing string (823*b*)

that is placed in one side of the third phalange sense part (823) and the fixing hanger (823c) that is placed in the other side of the third phalange sense part (823). The fixing string (823b) wraps the third phalange of the finger and is hung on the fixing hanger (823c). The fixing string (823b) can be made of elastic materials or stretchable materials.

The third phalange sense parts (823, 833, 843, 853) sense the movements of the distal phalanges of each finger of the user. To this end, the third phalange sense parts (823, 833, 843, 853) include the IMU sensors (825a, 835a, 845a, 855a) mounted in the printed circuit board as illustrated in FIG. 15. The IMU sensors can be 9-axis sensors based on MEMS.

According to another exemplary embodiment, the third phalange sense parts (823, 833, 843, 853) may include acceleration sensors instead of the IMU sensors. The acceleration sensors, for example, can be 3-axis acceleration sensors.

According to another exemplary embodiment, the third phalange sense parts (823, 833, 843, 853) may include acceleration sensors and gyroscope sensors instead of the IMU sensors. Here, the acceleration sensors can be 3-axis acceleration sensors and the gyroscope sensors can be 3-axis gyroscope sensors.

The third phalange sense parts (823, 833, 843, 853) are connected to the second phalange sense parts (822, 832, 842, 852) via the third connection parts (826, 836, 846, 856). In some embodiments, a connector (not illustrated) is placed in the printed circuit board of the third phalange sense parts (823, 833, 843, 853) and this connector is connected to one ends of the third connection parts (826, 836, 846, 856). The other ends of the third connection parts (826, 836, 846, 856) are connected to the connector (not illustrated) placed in the printed circuit board of the second phalange sense parts (822, 832, 842, 852).

According to some embodiments, at least one of the length, shape, and materials of third connection parts (826, 836, 846, 856) can be determined in a way that they do not hinder the movements of the fingers as can be seen in the first connection parts (813, 823, 833, 843, 853) or the second connection parts (814, 824, 834, 844, 854).

Meanwhile, unlike the device for rehabilitation exercise of the right hand (100R) illustrated in FIG. 2 or FIG. 4, the sense part for the wrist (870) of the device for rehabilitation exercise of the right hand (800R) illustrated in FIG. 13 or FIG. 15 is connected to the sense part for the back of the hand (860) via the fourth connection part (875). The fourth connection part (875) is used to transmit the movement data sensed in the sense part for the wrist (870) to the sense part for the back of the hand (860). Therefore, unlike the sense part for the wrist (170) in FIG. 4, the sense part for the wrist (870) in FIG. 15 has the IMU sensor (871), the control part (873), the voltage regulator part (874) only and may not have the transmission part (172) to send movement data. Here, the IMU sensor (871) can be replaced with an acceleration sensor or with an acceleration sensor and a gyroscope sensor.

Likewise, unlike the sense part for the back of the hand (160) in FIG. 4, the sense part for the back of the hand (860) in FIG. 13 may have the IMU sensor (861), the control part (863), the voltage regulator part (864), and the communication part (865) only and may not have the receiving part (162) to receive movement data. Here, the IMU sensor (861) can be replaced with an acceleration sensor or with an acceleration sensor and a gyroscope sensor.

So far, the device for rehabilitation exercise of the hand (800) in accordance with another exemplary embodiment has been explained in reference with FIG. 13 or FIG. 15.

According to the device for rehabilitation exercise of the hand (800) in accordance with another exemplary embodiment, the phalange sense parts are located in each phalange of the fingers and movement data can be obtained per phalange, which helps acquire more accurate results of rehabilitation exercise of the hands.

As is apparent from the above description, the movements of the hands can be sensed more accurately since sensor parts are located in each part of the hands.

The sensor parts located in each part of the hands are connected by cables and therefore, in case any sense part breaks down, the malfunctioning sense part can be replaced easily and quickly.

In case part of the sense parts is out of order, the malfunctioning sense part can be replaced and there is no need to replace the device for rehabilitation exercise of the hands, which would reduce maintenance cost of the device.

While exemplary embodiments have been particularly shown and described, it will be understood by those of ordinary skill in the art that various changes in form and details may be made therein without departing from the spirit and scope of the present inventive concept as defined by the following claims.

What is claimed is:

1. A device for rehabilitation exercises of user's hands, the device comprising:
    multiple sense parts configured to be located on parts of a hand, and configured to sense movements of the parts; and
    a communication part configured to send multiple pieces of movement data sensed by the multiple sense parts to an output device,
    wherein the multiple sense parts include:
        at least one finger sense part configured to be located on fingers of the hand, including a movement sensing sensor, and configured to measure and generate first movement data of the fingers;
        a back sense part configured to be located on a back of the hand, including a movement sensing sensor, and configured to measure and generate second movement data of the back of the hand; and
        a wrist sense part configured to be located on a wrist of the hand, including a movement sensing sensor, and configured to measure and generate third movement data of the wrist of the hand,
    wherein the finger sense part, the back sense part, and the wrist sense part include fixing tools configured to fix the finger sense part, the back sense part, and the wrist sense part to corresponding portions of the parts,
    wherein the finger sense part is connected to the back sense part by a connecting part,
    wherein each of the movement sensing sensor of the finger sense part, the movement sensing sensor of the back sense part, the movement sensing sensor of the wrist sense part includes at least one of an IMU (Inertial Measurement Unit) sensor, an acceleration sensor, and a gyroscope sensor,
    wherein the output device includes a screen and is configured to display, on the screen, a graphic object corresponding to the multiple pieces of movement data including the first movement data, the second movement data, and third movement data, and
    wherein the graphic object is configured to be displayed by using a correlation between the first movement data and the second movement data and a correlation between the second movement data and the third movement data.

2. The hand rehabilitation exercise device of claim 1, wherein the IMU sensor is a 9-axis IMU sensor.

3. The hand rehabilitation exercise device of claim 1, wherein the fixing tool located in the finger sense part includes:
- a fixing string placed on one side of the corresponding finger sense part to surround a portion of the corresponding finger at which the corresponding finger sense part is located; and
- a fixing hanger placed on an opposite side of the corresponding finger sense part such that one end of the fixing string is caught by the fixing hanger.

4. The hand rehabilitation exercise device of claim 1, wherein the back sense part further includes:
- an output part, and
- wherein the output part compares the movement data detected by the multiple sensing parts and reference movement data stored in advance to output an alarm signal that informs that the movement of the hand of the user does not reach a reference when the sensed movement data does not coincide with the reference movement data.

5. The hand rehabilitation exercise device of claim 4, wherein the output part is disposed in each of the parts of the hand.

6. The hand rehabilitation exercise device of claim 1, wherein the connecting part is separable from the finger sense part and the back sense part.

* * * * *